United States Patent
Hultgren et al.

(10) Patent No.: US 7,245,750 B2
(45) Date of Patent: Jul. 17, 2007

(54) METHOD AND APPARATUS FOR AUTOMATICALLY DETERMINING THE LOCATION OF INDIVIDUAL TEETH WITHIN ELECTRONIC MODEL IMAGES

(75) Inventors: Bruce Willard Hultgren, Victoria, MN (US); Timothy W. Vadnais, Victoria, MN (US); Michael Craig Marshall, Savage, MN (US); Grant James Cermak, Minneapolis, MN (US)

(73) Assignee: Geodigm Corporation, Chanhassen, MN (US)

( * ) Notice: Subject to any disclaimer, the term of this patent is extended or adjusted under 35 U.S.C. 154(b) by 711 days.

(21) Appl. No.: 10/350,304

(22) Filed: Jan. 22, 2003

(65) Prior Publication Data

US 2003/0231805 A1    Dec. 18, 2003

Related U.S. Application Data

(60) Provisional application No. 60/351,271, filed on Jan. 22, 2002.

(51) Int. Cl.
G06K 9/00 (2006.01)
(52) U.S. Cl. .................... 382/128; 128/922; 378/4
(58) Field of Classification Search ............. 382/100, 382/128; 128/922; 378/4
See application file for complete search history.

(56) References Cited

U.S. PATENT DOCUMENTS

| | | | | |
|---|---|---|---|---|
| 5,431,562 A | | 7/1995 | Andreiko et al. | |
| 5,605,459 A | * | 2/1997 | Kuroda et al. | 433/214 |
| 5,879,158 A | * | 3/1999 | Doyle et al. | 433/24 |
| 6,143,003 A | * | 11/2000 | Cosman | 606/130 |
| 6,371,761 B1 | | 4/2002 | Cheang et al. | |
| 6,409,504 B1 | * | 6/2002 | Jones et al. | 433/24 |
| 6,450,807 B1 | * | 9/2002 | Chishti et al. | 433/24 |
| 6,632,089 B2 | | 10/2003 | Rubbert et al. | |
| 6,648,640 B2 | | 11/2003 | Rubbert et al. | |
| 6,688,886 B2 | | 2/2004 | Hughes et al. | |
| 2003/0224316 A1 | | 12/2003 | Marshall | |
| 2004/0029078 A1 | | 2/2004 | Marshall | |
| 2004/0066877 A1 | * | 4/2004 | Arai et al. | 378/4 |

* cited by examiner

Primary Examiner—Vikkram Bali
Assistant Examiner—Anand Bhatnagar
(74) Attorney, Agent, or Firm—Merchant & Gould P.C.

(57) ABSTRACT

The method and apparatus provides a system for automatically determining the location of individual teeth within an electronic model image of a patients mouth. The electronic model image allows for manipulation of the electronic model image by end users. Possible horizontal cut lines are determined within a horizontal plane cut through the electronic model image corresponding to possible separation lines between the teeth. Possible vertical cut lines are then determined within a vertical plane cut through the electronic model image corresponding to possible separation lines between teeth. The system then automatically determines the locations of individual teeth using the possible horizontal cut lines and the possible vertical cut lines.

20 Claims, 8 Drawing Sheets

METHOD AND APPARATUS FOR AUTOMATICALLY DETERMINING THE LOCATION OF INDIVIDUAL TEETH WITHIN ELECTRONIC MODEL IMAGES

This application claims priority from provisional application Ser. No. 60/351,271, filed Jan. 22, 2002, and which is incorporate herein by reference.

TECHNICAL FIELD

The invention relates generally to a distributed computing system for the creation and distribution of electronic models of objects and more particularly to a system, method and article of manufacture for automatic determination of the location of individual teeth within an electronic model image of a patient's mouth to allow the manipulation of the electronic model images by end users.

BACKGROUND

Computational resources available for use by various end users of computing systems has increased significantly. This increase in capability of systems has created the ability for many more end users to utilize computer based image systems to replace processes that utilize paper and physical model processes. In the past, computer aided design, drafting, and manufacture (CAD/CAM) tools represented an area of applications in which computer based image systems have migrated from paper and model based processes to electronic systems.

These CAD/CAM system typically consist of design and drafting tools that allow technical designers to build systems that were previously designed on paper using draftsmen. Over time, the computing system and their respective tools have allowed increasing interactive manipulation of components during the design process. This advance in design of items that are then manufactured has occurred using these computer aided systems.

These CAD/CAM systems, however, typically start their processes with a set of pre-defined libraries of components that may be used by the user of the computing system. For example, electronic schematics possess a library of components that are used to specify a circuit and its layout. The creation of these libraries, as well as the amount of computational resources needed to perform the operations related to these systems, has prevented the widespread use of these systems in other areas of technology.

With the advances recently made computational systems, these computer based image systems may be used to permit end users to replace paper and physical models with electronic images. Two areas of technology present additional obstacles to the more wide-spread use of these systems. First, a mechanism to capture image representations of physical objects accurately and with sufficient resolution is needed in a form that is both inexpensive to operate while providing rapid turn-around for users. Second, a mechanism to easily separate the electronic model into its separate components. This problem is especially acute when impressions of human teeth are to be scanned to allow electronic images of the models of a patient's teeth to be represented and manipulated as individual teeth. Neither of these latter obstacles have been overcome in existing imaging systems.

SUMMARY

The present invention relates to a method, apparatus, and article of manufacture for providing.

A system in accordance with the principles of the present invention includes a computing system.

Other embodiments of a system in accordance with the principles of the invention may include alternative or optional additional aspects. One such aspect of the present invention is a method and computer data product encoding instructions for automatically determining the location of individual teeth within an electronic model image of a patient's mouth to allow the manipulation of the electronic model images by end users. The method determines possible horizontal cut lines within a horizontal plane cut through the electronic model image corresponding to possible separation lines between teeth, determines possible vertical cut lines within a vertical plane cut through the electronic model image corresponding to possible separation lines between teeth, and automatically determines the locations of individual teeth using the possible horizontal cut lines and the possible vertical cut lines.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there are illustrated and described specific examples of an apparatus in accordance with the invention.

DETAILED DESCRIPTION

The present invention relates to a code generation method, apparatus, and article of manufacture for providing a distributed computing system for the creation and distribution of electronic models of objects including a system, method and article of manufacture for automatic determination of the location of individual teeth within an electronic model image of a patient's mouth to allow the manipulation of the electronic model images by end users.

Figure 1A:
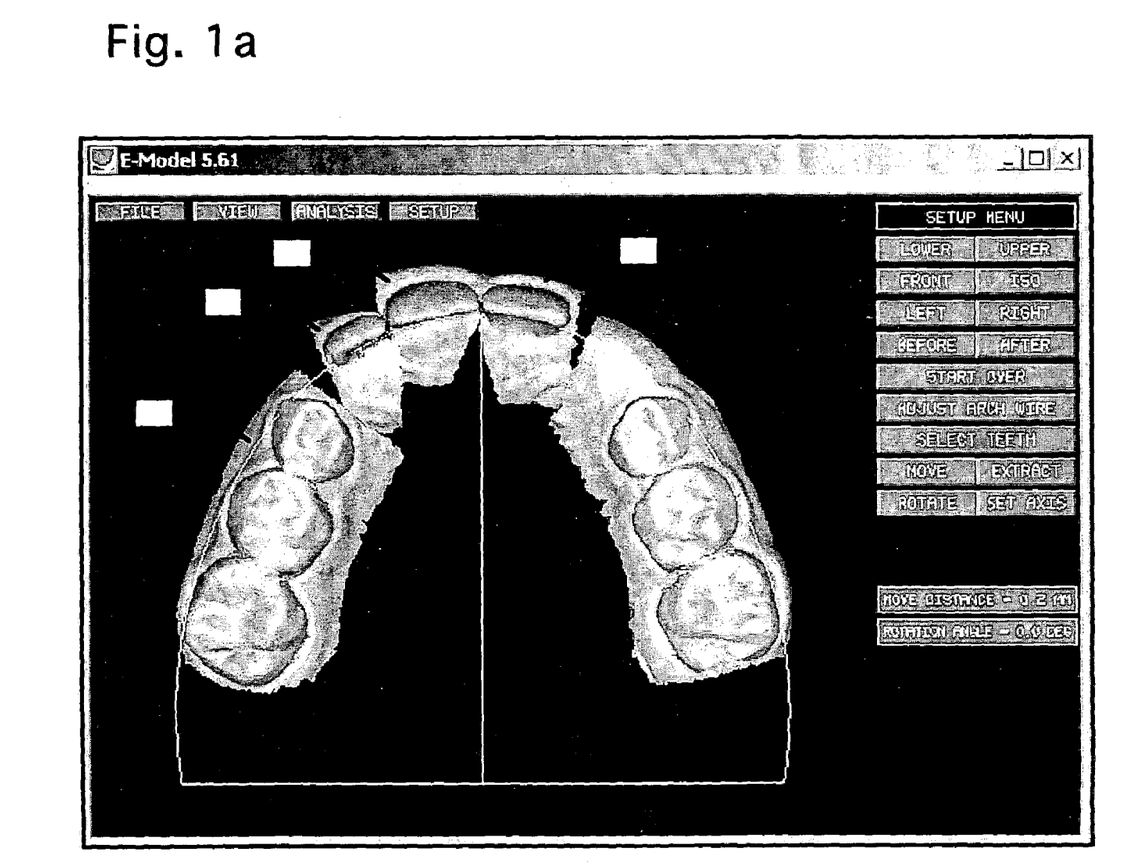
FIG. 1a illustrates an electronic model image of a patient's mouth in which individual teeth have been identified and moved locations in support of a plan of treatment according to one embodiment of the present invention.

FIG. 1a illustrates an electronic model image of a patient's mouth in which individual teeth have been identified and moved locations in Support of a plan of treatment according to one embodiment of the present invention. An electronic model of a patent's upper teeth are shown 101 in which individual teeth 111–113 have been electronically moved to allow a dental practitioner to visualize the treatment plan. In order for this process to occur, two events must occur. First, an electronic model for the teeth must be generated. This occurs when a physical mold or impression of the mouth is generated. This impression is then electronically scanned to generate the model. The process for generating an electronic model for the teeth is described in commonly assigned U.S. patent application entitled "METHOD AND APPARATUS FOR ELECTRONIC DELIVERY OF DENTAL IMAGES", Ser. No. 09/846037 filed April 2001 which is incorporated by reference.

Once the electronic model has been generated for the impression, the locations of the individual teeth need to be determined. This location identification may occur using manually specified locations entered into a computing system by a user. Alternatively, these locations may be automatically determined using information contained within the electronic model. Once the locations of the teeth are known, the electronic model may be cut into a set of individual teeth images 111–113 that may be manipulated on a computer display device.

Figure 1B:
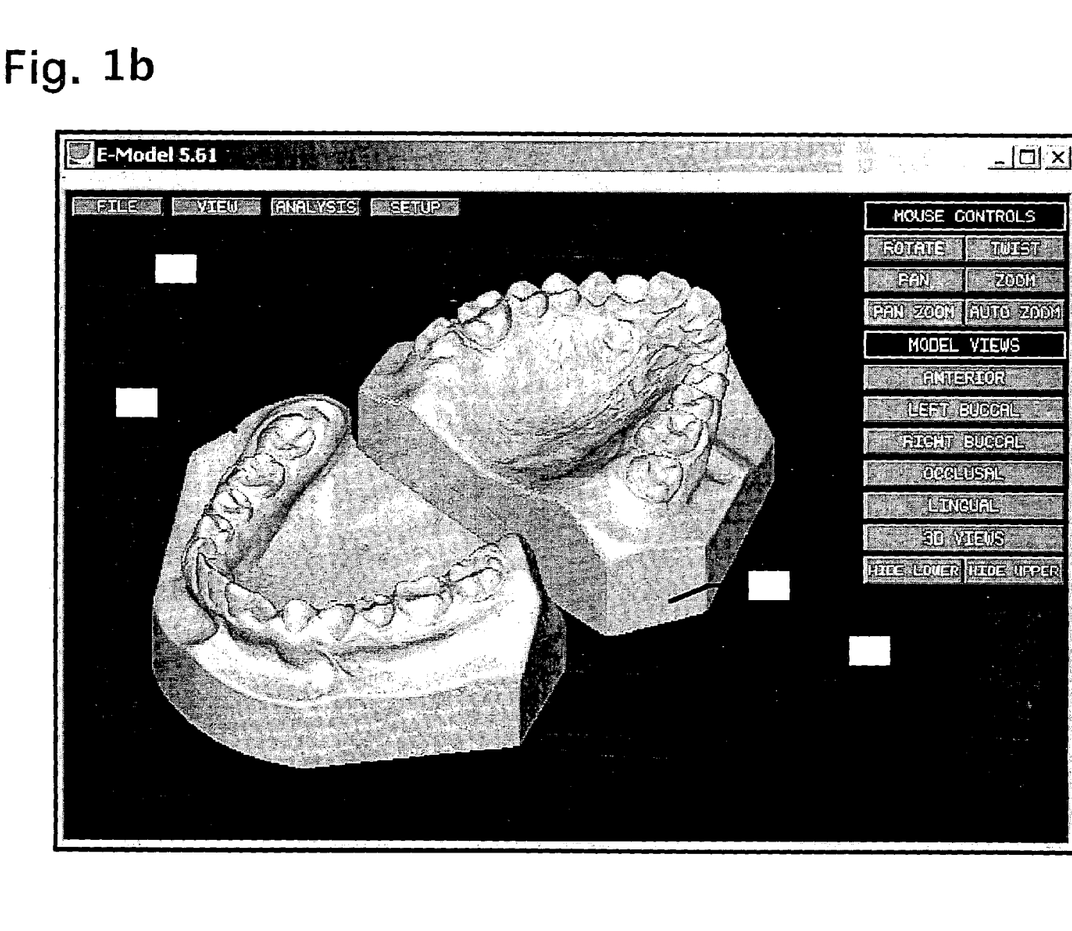
FIG. 1b illustrates an electronic model image of a patient's mouth useful for implementing an embodiment of the present invention.

FIG. 1b illustrates an electronic model image of a patient's mouth useful for implementing an embodiment of the present invention. The electronic model image for a patient's mouth is typically constructed using two model components, an upper teeth section 104 and a lower teeth section 103. Both of these teeth sections themselves include teeth model elements, gum model elements, and a model base element. The model base element is added to the model when it is generated to aid in the spatial registration of the upper teeth section 104 and the lower teeth 103 section relative to each other as the teeth appear in the patient's mouth. When the location of individual teeth are determined only one of the two teeth sections are processed at any given time.

Figure 2:
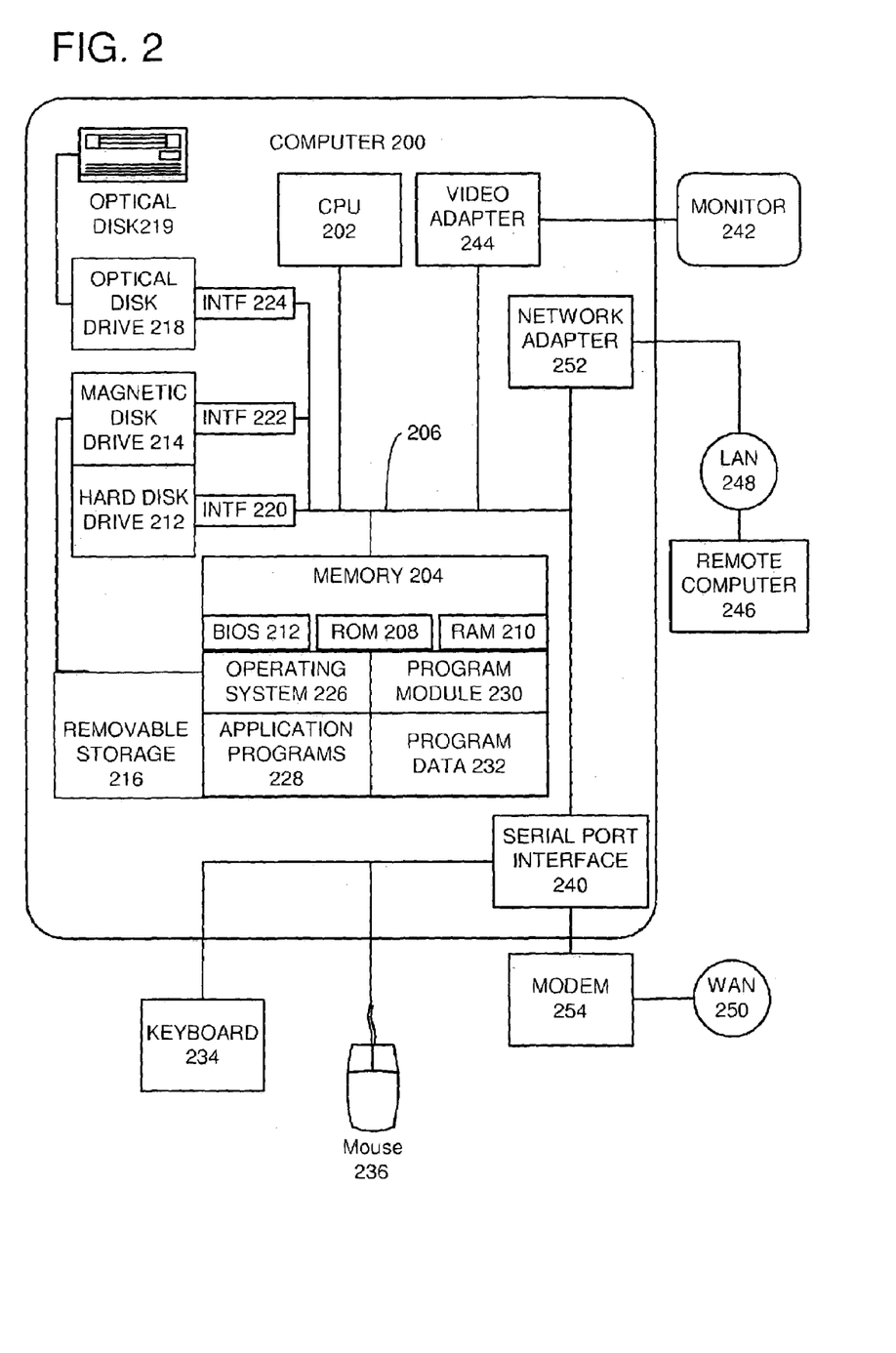
FIG. 2 illustrates an exemplary computing system useful for implementing an embodiment of the present invention.

With reference to FIG. 2, an exemplary system for implementing the invention includes a general-purpose computing device in the form of a conventional personal computer 200, including a processor unit 202, a system memory, 204 and a system bus 206 that couples various system components including the system memory 204 to the processor unit 202. The system bus 206 may be any of several types of bus structures including a memory bus or memory controller, a peripheral bus and a local bus using any of a variety of bus architectures. The system memory includes read only memory (ROM) 208 and random access memory (RAM) 210. A basic input/output system 209 (BIOS), which contains basic routines that help transfer information between elements within the personal computer 200, is stored in ROM 208.

The personal computer 200 further includes a hard disk drive 212 for reading from and writing to a hard disk, a magnetic disk drive 214 for reading from or writing to a removable magnetic disk, and an optical disk drive 218 for reading from or writing to a removable optical disk such as a CD ROM, DVD, or other optical media. The hard disk drive 212, magnetic disk drive 214, and optical disk drive 218 are connected to the system bus 206 by a hard disk drive interface 220, a magnetic disk drive interface 222, and an optical drive interface 224, respectively. The drives and their associated computer-readable media provide nonvolatile storage of computer readable instructions, data structures, programs, and other data for the personal computer 200. The computer 200 can also include removable storage 216.

Although the exemplary environment described herein employs a hard disk, a removable magnetic disk, and a removable optical disk, other types of computer-readable media capable of storing data can be used in the exemplary system. Examples of these other types of computer-readable mediums that can be used in the exemplary operating environment include magnetic cassettes, flash memory cards, digital video disks, Bernoulli cartridges, random access memories (RAMs), and read only memories (ROMs).

A number of program modules may be stored on the hard disk, magnetic disk, optical disk, ROM 208 or RAM 210, including an operating system 226, one or more application programs 228, other program modules 230, and program data 232. A user may enter commands and information into the personal computer 200 through input devices such as a keyboard 234 and mouse 236 or other pointing device. Examples of other input devices may include a microphone, joystick, game pad, satellite dish, and scanner. These and other input devices are often connected to the processing unit 202 through a serial port interface 240 that is coupled to the system bus 206. Nevertheless, these input devices also may be connected by other interfaces, such as a parallel port, game port, or a universal serial bus (USB). A monitor 242 or other type of display device is also connected to the system bus 206 via an interface, such as a video adapter 244. In addition to the monitor 242, personal computers typically include other peripheral output devices (not shown), such as speakers and printers.

The personal computer 200 may operate in a networked environment using logical connections to one or more remote computers, such as a remote computer 246. The remote computer 246 may be another personal computer, a server, a router, a network PC, a peer device or other common network node, and typically includes many or all of the elements described above relative to the personal computer 200. The network connections include a local area network (LAN) 248 and a wide area network (WAN) 250. Such networking environments are commonplace in offices, enterprise-wide computer networks, intranets, and the Internet.

When used in a LAN networking environment, the personal computer 200 is connected to the local network 248 through a network interface or adapter 252. When used in a WAN networking environment, the personal computer 200 typically includes a modem 254 or other means for establishing communications over the wide area network 250, such as the Internet. The modem 254, which may be internal or external, is connected to the system bus 206 via the serial port interface 240. In a networked environment, program modules depicted relative to the personal computer 200, or portions thereof, may be stored in the remote memory storage device. It will be appreciated that the network connections shown are exemplary, and other means of establishing a communications link between the computers may be used.

Additionally, the embodiments described herein are implemented as logical operations performed by a computer. The logical operations of these various embodiments of the present invention are implemented (1) as a sequence of computer implemented steps or program modules running on a computing system and/or (2as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Figure 3A:
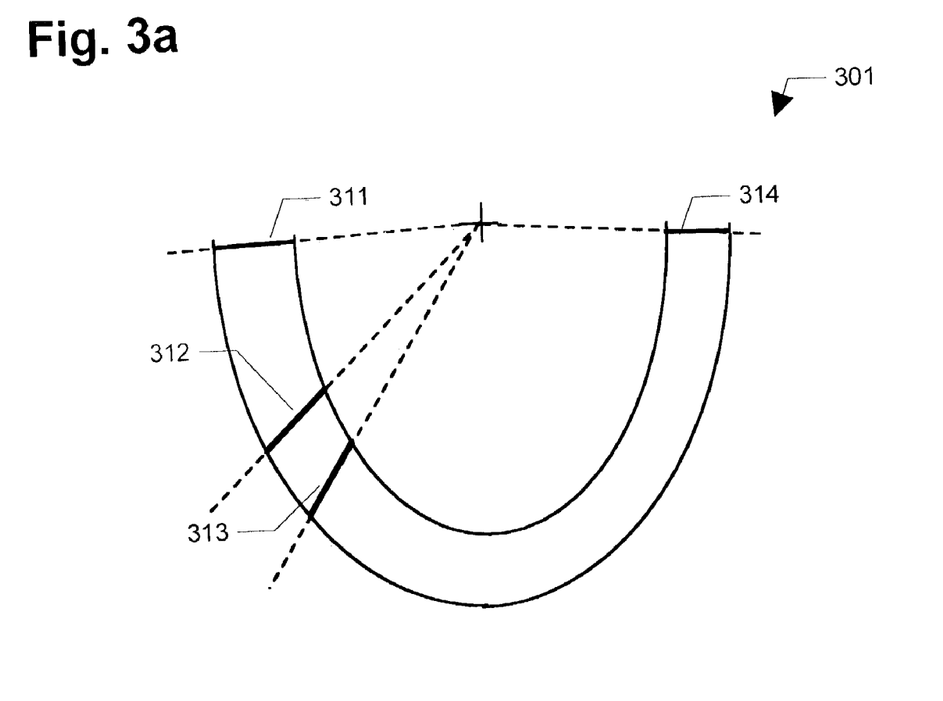
FIG. 3a–b illustrate horizontal processing elements determined from the electronic model image to identify locations of individual teeth according to an embodiment of the present invention.
Figure 3B:
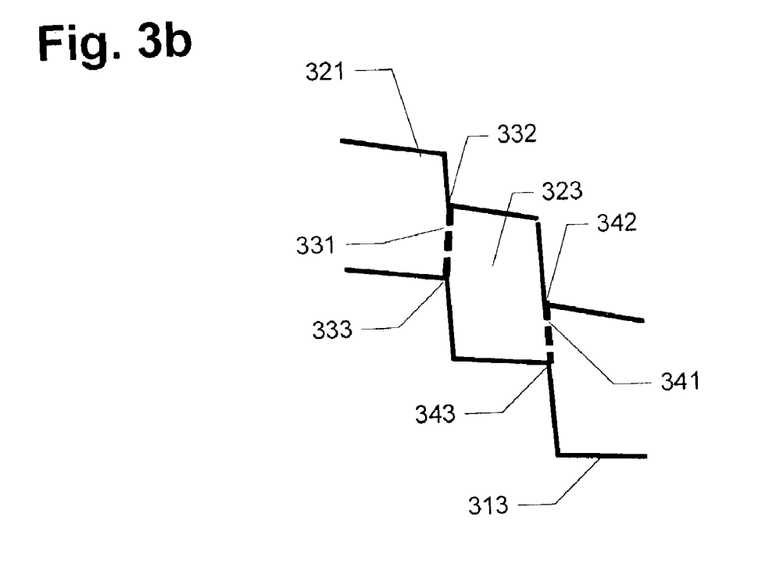

FIG. 3a–b illustrate horizontal precessing elements determined from the electronic model image to identify locations of individual teeth according to an embodiment of the present invention. In order to identify the locations of individual teeth, horizontal processing of the electronic model image may occur. First, a horizontal plane is determined through the middle of the electronic model image. This horizontal plane is at a location between the highest most point of the image, which would represent a point on a crown of a tooth, and the model base element which has been added to the impression of the teeth. The resultant 2D image of the electronic model is shown in FIG. 3a. The model of the teeth 301 generally follow an elliptical curve that rotates about a center point. The model is typically bound at either end 311,314 at points corresponding to the edge of the back two teeth, 311, 314. The separation of teeth in the middle of the model are specified using cut lines 312 and 313 located on either side of a tooth 315. The separation of these two cut lines 312 313 is known to be a distance greater than a minimum horizontal separation distance.

This minimum horizontal separation distance may be a fixed minimum number for all patients as all teeth are expected to be greater than some minimum size. This minimum horizontal separation distance may also be a specified minimum size based upon the known size of the patient's mouth. This variation will account for scaling of minimum tooth sizes based upon the general idea that individual patient's with larger mouths will generally possess larger teeth. Additionally, the minimum horizontal separation distance may also be determined by using knowledge of the type of teeth known to exist in various portions of the mouth. For example, teeth that are expected to be located between back edge 311 and cut line 312 would typically be molars. Teeth expected in the center of the model would typically be incisors. These types of teeth are known to possess different sizes and shapes; as such, these known differences may be used to vary the minimum horizontal separation distance when determining cut lines between teeth.

FIG. 3b illustrates a small segment of the horizontal plane cut through the electronic model image. In this subset image, the model consists of an inner image surface 321 and an outer image surface 313. An individual tooth 323 may be identified using a left cut line 331 and a right line 341. The left cut line 331 may be specified by locating two end points 332 and 333 in which the distance between the inner image surface 321 and the outer image surface 322 are locally minimum distances. In some cases, a horizontal plane may be cut at a location in which a individual tooth is not near or touching another tooth. When this occurs these local minimum distances will be zero. When teeth are close or touching each other, the cut lines are needed to segment the teeth into separate elements in the electronic model image.

The process of looking for these locally minimum distances may be performed at several horizontal height locations between the model base element and the tooth peaks. By finding cut lines at various horizontal locations, separation planes between the teeth may be specified. These various cuts should be made a locations that are centered upon the known spacing between the model base element and the peak of the teeth. If the horizontal cut is made close to the model base element, many teeth may be located so close together that accurate separation of the teeth may not be possible. If the horizontal cut is made too close to the peak of the teeth, features of the crowns of the teeth may be mistaken for separation between the teeth.

Figure 4A:
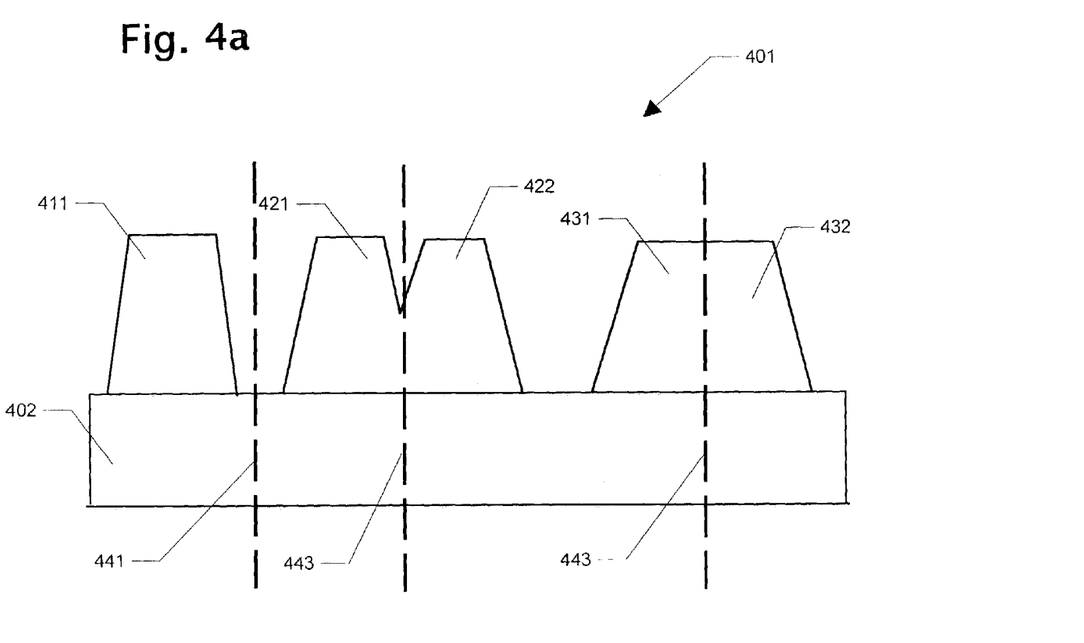
FIG. 4a–b illustrate vertical processing elements determined from the electronic model image to identify locations of individual teeth according to an embodiment of the present invention.
Figure 4B:
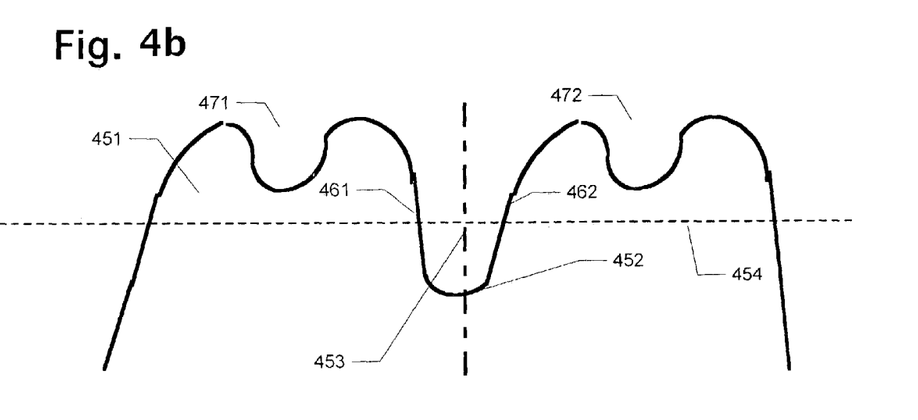

FIGS. 4a–b illustrate vertical processing elements determined from the electronic model image to identify locations of individual teeth according to an embodiment of the present invention. Similar to the horizontal processing, vertical analysis of the model data may that is viewed along a vertical cut made through an elliptical arc through the module may also permit the automatic determination of teeth separation cut lines. FIG. 4a illustrates a sequence of teeth having various relation ships to neighboring teeth. Tooth 411, which is located on model base element 402, is shown to be completely separate from its neighboring tooth 421. In such a situation, cut line 441 between tooth 411 and tooth 421 may be easily determined by locating the local minimum 452 (FIG. 4b) for a vertical location along an upper surface of the model between tooth 411 and 421. This situation is shown in more detail in FIG. 4b where cut line 453 is made at the local minimum 452 between tooth 451 and tooth 455. In this first situation, the local minimum 452 is easily recognized as a cut line as the local minimum is located at the patient's gums and as such is located close to the model base element 402.

A similar situation may arise in determining cut line 443 between tooth 421 and tooth 422. In this situation, the two teeth are closer together. As a result, the two teeth touch each other at a point mid way between the teeth peaks and the gum line. When this situation is compared to cut line 441, the same results shown in FIG. 4b occur. The only difference between these situations is that the location of the local minimum 452 will be higher than the prior case but may still be recognized if the local minimum is below threshold 454.

A third possible situation may arise as is illustrated by cut line 445 located between tooth 431 and tooth 432. In this situation, no discernible separation between the two teeth is seen as they are completely overlapping each other. This situation occurs when the local minimum 452 between two teeth is located above a threshold 454 such that it cannot be distinguished between local features of the teeth crowns 471–472. In this situation, the cut line 445 may be determined less accurately by determining a point estimated to be between tooth 431 and 432.

If a system combines the cut lines determined using both the horizontal element processing shown in FIG. 3 and the vertical processing shown in FIG. 4, all of the cut lines between teeth in an electronic model image may be determined. When the horizontal element processing and the vertical element processing find cut lines that are identical, the cut line is know to be correct with a high degree of certainty. When a high level of confidence may be given to a cut line from either horizontal or vertical processing but not both, an accurate cut line may still be determined with a degree of certainty. Only when both horizontal and vertical processing cannot determine a location of a cut line with a high level of confidence must additional information be considered.

Once many of the locations of teeth are determined using just the vertical and horizontal processing described above, the locations of other teeth may be estimated using additional information. For example, if the number of teeth known to be present is considered, the number of teeth not found using the above process may be determined. The locations of the known teeth may suggest regions where no known teeth were found. Using these additional pieces of information may allow the remaining possible cut lines found in the horizontal and vertical processing to be ranked to locate the most likely location in a region where teeth were not found to propose the most likely remaining cut line locations.

Figure 5:
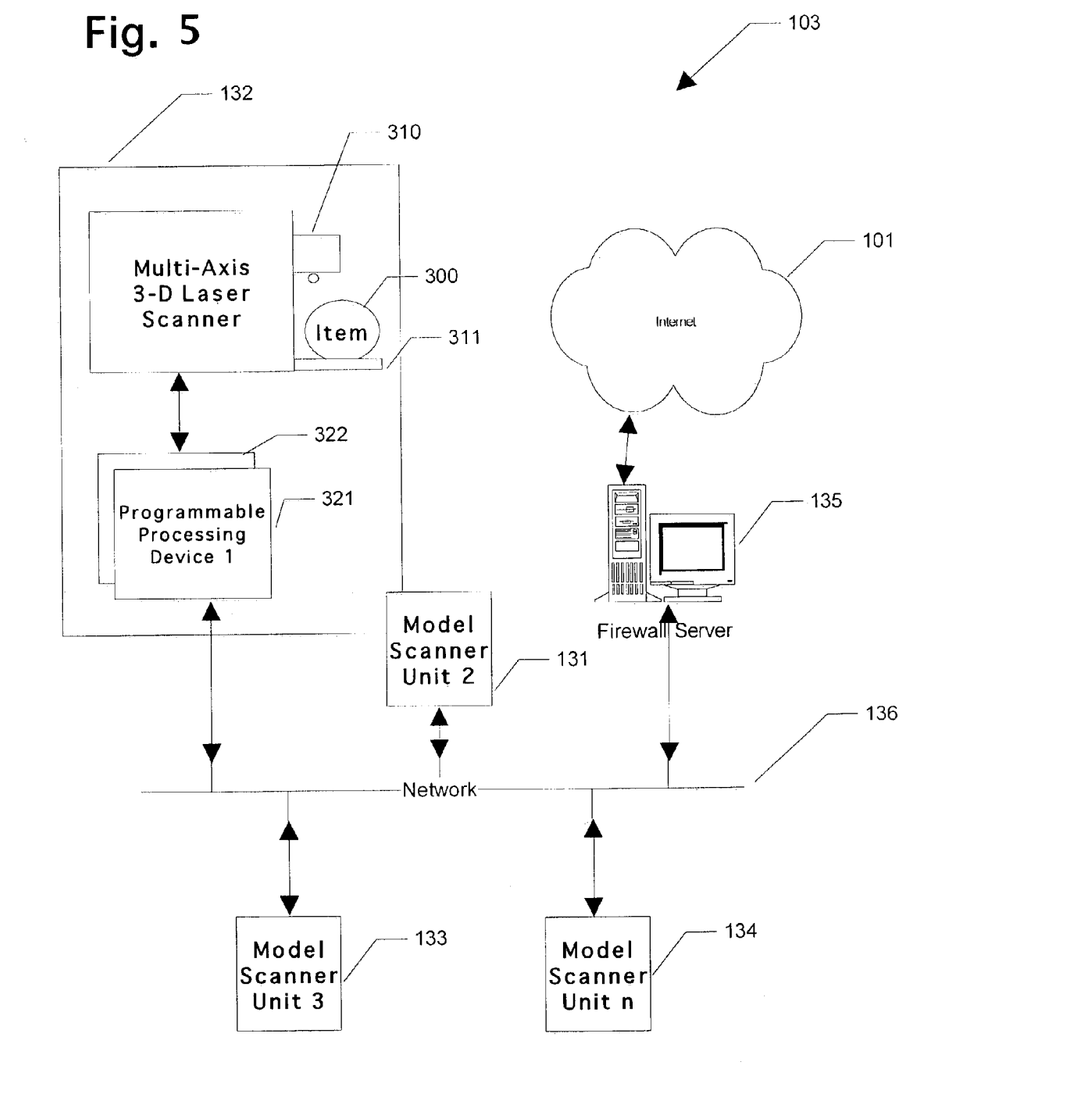
FIG. 5 illustrates a distributed computing system for the creation and distribution of electronic models of objects according to one embodiment of the present invention.

FIG. 5 illustrates a distributed computing system for the creation and distribution of electronic model images of objects according to one embodiment of the present invention. End users operate a plurality of different computing systems 110–113 to perform their respective computing tasks. End users typically use one general purpose computing system for a variety of tasks. In order for use of imaging systems to replace paper and model based systems, the imaging system used by end users 110–113 consist of laptop and desktop computing systems.

These computing systems typically possess a mechanism to communicate with other computing systems over a communications network 101. The Internet 101, as a publicly available communications network, provides an available communications path between virtually any two computing systems after they first connect to the Internet. While other communications mechanisms exist and may be used, the Internet provides a well-known mechanism to communicate data between two computing systems.

In an image-based electronic model image system, an end user 110 communicates over a communications network 101 to a server 121 to retrieve electronic eModels from a database 122. The end user 122 may be located anywhere a connection to the communications network 101 exists to retrieve the eModels from the database 122. This database 122 may be located within an eModel data server system 102 that is maintained by third-parties that provide maintenance, data back-up, and similar data processing overhead functions that are not an overriding concern for an end user. This data back-up, for example, may consist of long-term archiving of data to replace maintenance of physical models that have in the past required a great deal of effort and expense to complete.

The electronic model images themselves consist of a data file stored on the server 121 in a database 122 that allows quick and efficient access for users. These electronic model images are generated in a separate electronic model image generation system 103 that consists of one or more model scanning units 131–134. These units 131–134 are connected together using a local communications network 136 and a communications path 135 to the Internet 101. As such, electronic model images, once generated may be transferred to the electronic model image Data server system 102 for ultimate use by end users 110–113.

Figure 6:
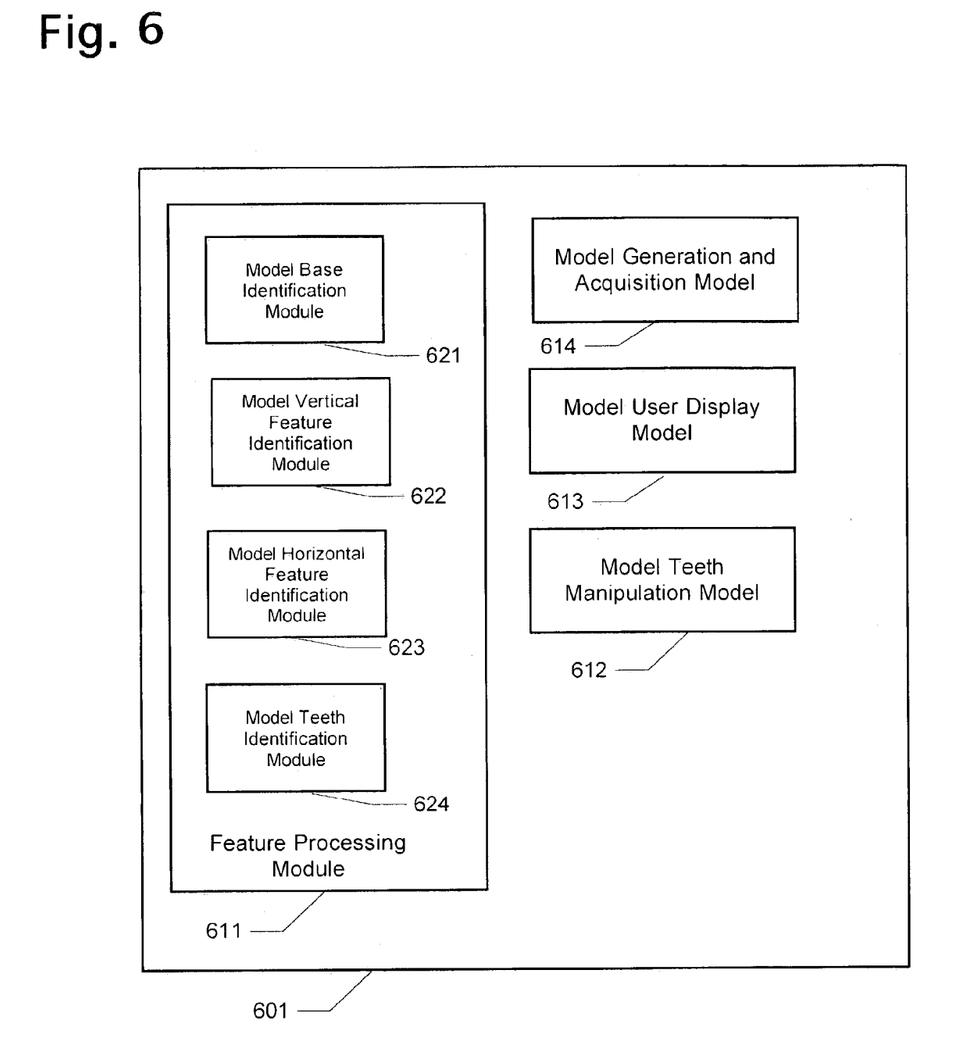
FIG. 6 illustrates a block diagram for an tooth location determination processing system according to an embodiment of the present invention.

FIG. 6 illustrates a block diagram for an tooth location determination processing system according to an embodiment of the present invention. A computer implemented system 601 used to process electronic model images includes several processing modules including a feature processing module 611, a model generation and acquisition module 614, a module user display module 613 and a model teeth manipulation module 612. The feature processing module 611 itself includes a model base identification module 621, a model vertical feature identification module 622, a model horizontal feature identification module 623, and a module teeth identification module 624. The model generation and acquisition module 614 is used to generate and obtain electronic model images from remote storage for use in processing within the system 601. The module user display module 613 outputs the electronic model images onto a computer display device for viewing by a user of the system 601. The model teeth manipulation module 612 is used by an end user of the system to obtain measurements relating to the electronic model as well as manipulate the location of teeth when a proposed treatment plan for a patient is considered as shown in FIG. 1a.

The model base identification module 621 is used to identify the model base element from teeth and gum data elements obtained from within the electronic model image. The model vertical feature identification module 622 performs the processing described above with reference to FIG. 4 in which vertical cut lines are identified. The model horizontal feature identification module 623 performs the processing described above with reference to FIG. 3 in which horizontal cut lines are identified. The module teeth identification module 624 performs the processing described above with reference to FIG. 4 in which vertical and horizontal cut lines are used to identify all of the teeth found within the electronic model image.

Figure 7:
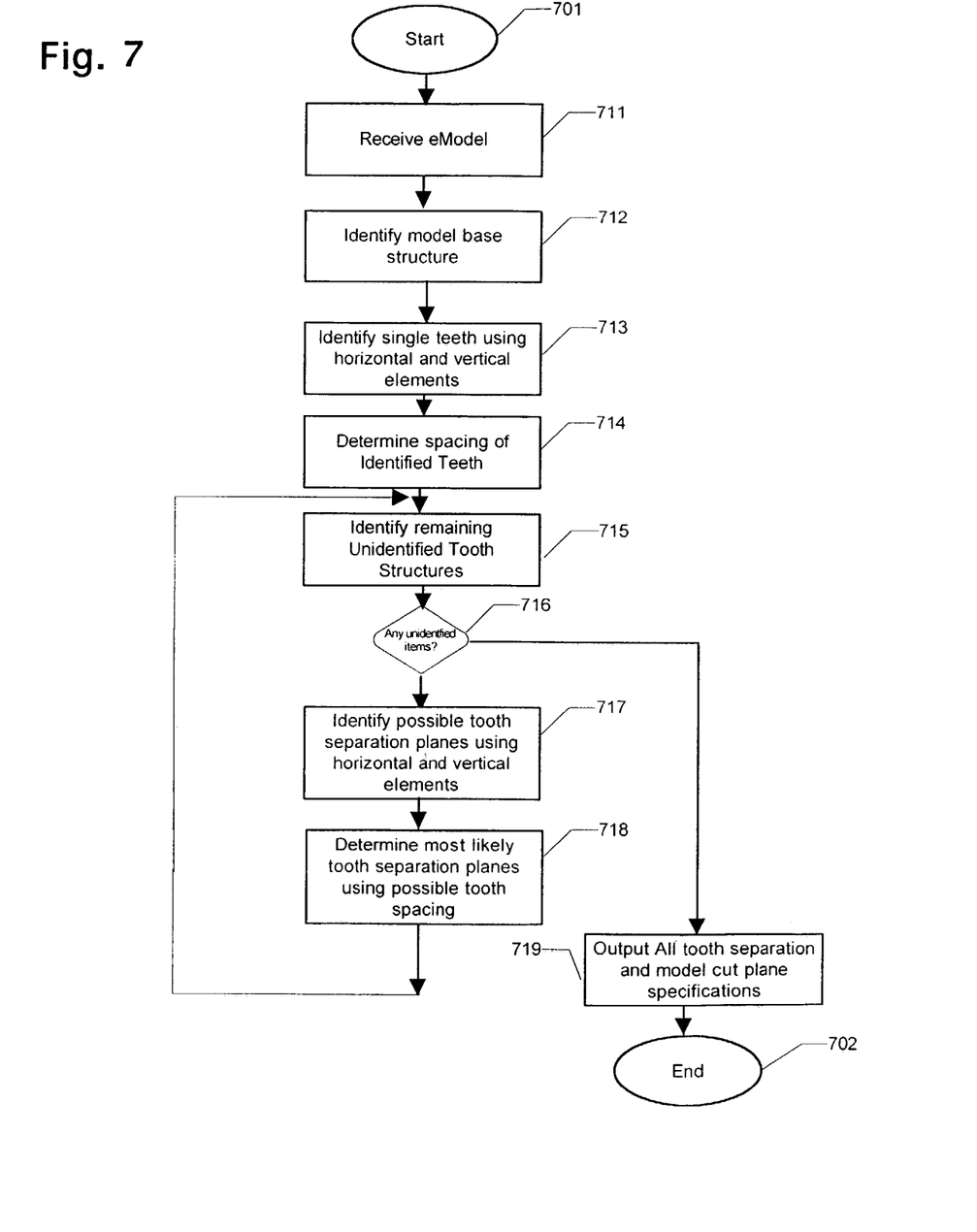
FIG. 7 illustrates an operational flow for determining the locations of teeth within an electronic model image according to yet another example embodiment of the present invention.

FIG. 7 illustrates an operational flow for determining the locations of teeth within an electronic model image according to yet another example embodiment of the present invention. The processing begins 701 and an electronic model image is obtained for use in the processing in module 711. In this module, the upper teeth section or lower teeth section are selected for separate processing. Once a appropriate teeth section is selected, module 712 identifies the model base element for use in generating vertical and horizontal cut lines.

Module 713 generates the horizontal and vertical cut lines and identifies single teeth that are known to be identified with a high degree of certainty. This high degree of certainty is known when either of a particular vertical cut line or a particular vertical cut line has been identified with a high level of confidence. This level of confidence may relate to a local minimum distance between horizontal cut lines being less than a specified value. Similarly, this level of confidence may relate to the local minimum used to define a vertical cut line being below a specified threshold. When the cut lines on both sides of a tooth are known to a high level of certainty, the tooth may be confidently identified.

Once some of the teeth are identified, module 714 determines the number and spacing of the known teeth. This spacing of the teeth may identify errors if teeth are found to be overlapping in location or are found to be less than a minimum size. This spacing may also be used to identify regions of the electronic model image where teeth have yet to be found.

These regions containing possible unidentified teeth are then searched in module 715 to identify the know vertical and horizontal structures that may represent addition cut lines. Using these identified structures, the most likely regions where the number of unidentified teeth may be found. Test module 716 determines if additional teeth need to be found. If not, module 719 outputs the specification of all found teeth and the electronic model cut planes that may be used to separate the module into a set of separate teeth images before the processing ends 702.

If test module 716 determines that additional teeth need to be identified, module 717 identifies possible tooth separation planes in likely regions where teeth have not still been found using the previously identified possible vertical and horizontal cut lines. The possible separation planes are ranked to find the most likely candidate in module 718. This candidate is used to identify a tooth before the regions of unidentified teeth are updated for use in further processing. Once a tooth is identified, the processing returns to test module 715 in an attempt to find additional teeth. The processing within this loop continues until all of the teeth are found.

FIG. 2 illustrates an example of a suitable operating environment 121 in which the invention may be implemented. The operating environment is only one example of a suitable operating environment 121 and is not intended to suggest any limitation as to the scope of use or functionality of the invention. Other well known computing systems, environments, and/or configurations that may be suitable for use with the invention include, but are not limited to, personal computers, server computers, held-held or laptop devices, multiprocessor systems, microprocessor-based systems, programmable consumer electronics, network PCs, minicomputers, mainframe computers, distributed computing environments that include any of the above systems or devices, and the like.

The invention may also be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed in desired in various embodiments.

A network server 121 typically includes at least some form of computer readable media. Computer readable media can be any available media that can be accessed by the network server 110. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, BC-ROM, digital versatile disks (DVD) or other optical storage, magnetic cassettes, magnetic tape, magnetic disk storage or other magnetic storage devices, or any other medium which can be used to store the desired information and which can be accessed by the network server 110.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

While the above embodiments of the present invention describe a network based processing system providing processing services to remote clients, one skilled in the art will recognize that the various distributed computing architectures may be used to implement the present invention as recited within the attached claims. It is to be understood that other embodiments may be utilized and operational changes may be made without departing from the scope of the present invention.

The foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. Thus the present invention is presently embodied as a method, apparatus, computer storage medium or propagated signal containing a computer program for providing a method, apparatus, and article of manufacture for providing a distributed computing system for the creation and distribution of electronic models of objects.

What is claimed is:

1. A computer implemented method of automatic determination of locations of individual teeth within an electronic model image of teeth of a patient to enable manipulation of the electronic model image by end users, the method comprising:
   determining possible horizontal cut lines within a horizontal plane cut through the electronic model image corresponding to possible separation lines between the teeth;
   determining possible vertical cut lines within a vertical plane cut through the electronic model image corresponding to possible separation lines between the teeth; and
   automatically determining locations of individual teeth using the possible horizontal cut lines and the possible vertical cut lines.

2. The method according to claim 1 wherein the method further comprises:
   obtaining the electronic model image by scanning a physical impression of the teeth of the patient;
   determining a model base element corresponding to a registration base that is part of the physical impression of the teeth of the patient; and
   cutting the electronic model image into a set of electronic model teeth images configured to be further manipulated by a user.

3. The method according to claim 2, wherein the horizontal plane cut through the electronic model image is located parallel to the model base element and is also located between the model base element and the top of the teeth.

4. The method according to claim 3, wherein the possible horizontal cut lines are located at locations where a minimum horizontal local separation distance is found for electronic model image data when measured relative to the two sides of the image data.

5. The method according to claim 4, wherein the minimum horizontal local separation distance is found for electronic model image data when the horizontal local minimum is below a specified separation distance.

6. The method according to claim 4, wherein the minimum horizontal local separation distance is found for electronic model image data when the horizontal local minimum is below a specified separation distance.

7. The method according to claim 2, wherein the vertical plane cut through the electronic model image is located perpendicular to the model base element and is also located along a parabolic arc through the teeth.

8. The method according to claim 7, wherein the possible vertical cut lines are located at locations where a vertical local minimum is found for electronic model image data when measured relative to the model base element.

9. The method according to claim 7, wherein the possible vertical cut lines are located at locations where a vertical local minimum is found for electronic model image data when measured relative to the model base element.

10. The method according to claim 8, wherein the vertical local minimum is found for electronic model image data when the vertical local minimum is below a specified threshold.

11. The method according to claim 8, wherein the vertical local minimum is found for electronic model image data when the vertical local minimum is below a specified threshold.

12. The method according to claim 2, wherein the method further comprises identifying regions of electronic image data where teeth have not been found;
   identifying possible teeth separation cut lines within the identified regions;
   ranking the possible teeth separation cut lines; and
   using the rankings of possible separation cut lines to identify teeth.

13. The method according to claim 12, further comprising continuing to search the regions of electronic image data where teeth have not been found until the number of identified teeth is greater than a specified number of teeth.

14. The method according to claim 12, further comprising continuing to search the regions of electronic image data where teeth have not been found until the number of identified teeth is greater than a specified number of teeth.

15. The method according to claim 2, wherein the vertical plane cut through the electronic model image is located perpendicular to the model base element and is also located along a parabolic arc through the teeth.

16. The method according to claim 2, wherein the method further comprises identifying regions of electronic image data where teeth have not been found;
   identifying possible teeth separation cut lines within the identified regions;
   ranking the possible teeth separation cut lines; and
   using the rankings of possible separation cut lines to identify teeth.

17. A computer program data product embedded in a computer readable medium for a computing system to implement a method of automatic determination of location of individual teeth within an electronic model image of teeth of a patient to enable manipulation of the electronic model image by end users, the method comprising:
   determining possible horizontal cut lines within a horizontal plane cut through the electronic model image corresponding to possible separation lines between the teeth;
   determining possible vertical cut lines within a vertical plane cut through the electronic model image corresponding to possible separation lines between the teeth; and
   automatically determining locations of individual teeth using the possible horizontal cut lines and the possible vertical cut lines.

18. The computer program data product according to claim 17, wherein the method further comprises:
   obtaining the electronic model image by scanning a physical impression of the teeth of the patient;
   determining a model base element corresponding to a registration base that is part of the physical impression of the teeth of the patient; and
   cutting the electronic model image into a set of electronic model teeth images configured to be further manipulated by a user.

19. The computer program data product according to claim 18, wherein the horizontal plane cut through the electronic model image is located parallel to the model base element and is also located between the model base element and the top of the teeth.

20. The computer program data product according to claim 19, wherein the possible horizontal cut lines are located at locations where a minimum horizontal local separation distance is found for electronic model image data when measured relative to the two sides of the image data.

* * * * *

UNITED STATES PATENT AND TRADEMARK OFFICE
CERTIFICATE OF CORRECTION

| | |
|---|---|
| PATENT NO. | : 7,245,750 B2 |
| APPLICATION NO. | : 10/350304 |
| DATED | : July 17, 2007 |
| INVENTOR(S) | : Hultgren et al. |

Page 1 of 1

It is certified that error appears in the above-identified patent and that said Letters Patent is hereby corrected as shown below:

Col. 1, line 9: "incorporate herein" should read --incorporated herein--

Col. 3, line 8: "locations in Support of a" should read --locations in support of a--

Col. 5, line 10: "horizontal precessing elements" should read --horizontal processing elements--

Signed and Sealed this

Sixth Day of May, 2008

JON W. DUDAS
*Director of the United States Patent and Trademark Office*